United States Patent
Barnes

(10) Patent No.: US 9,022,926 B2
(45) Date of Patent: May 5, 2015

(54) REINFORCED FLEXIBLE ACCESS ASSEMBLY

(75) Inventor: Andrew Barnes, Naugatuck, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/224,358

(22) Filed: Sep. 2, 2011

(65) Prior Publication Data

US 2012/0130183 A1  May 24, 2012

Related U.S. Application Data

(60) Provisional application No. 61/416,517, filed on Nov. 23, 2010.

(51) Int. Cl.
*A61B 1/32* (2006.01)
*A61B 17/34* (2006.01)

(52) U.S. Cl.
CPC ..... *A61B 17/3423* (2013.01); *A61B 2017/3445* (2013.01)

(58) Field of Classification Search
CPC ................ A61B 17/3423; A61B 2017/3429; A61B 2017/3445
USPC ................................................ 600/201–249
See application file for complete search history.

(56) References Cited

U.S. PATENT DOCUMENTS

| | | | |
|---|---|---|---|
| 5,312,417 A | 5/1994 | Wilk | |
| 5,391,156 A | 2/1995 | Hildwein et al. | |
| 5,788,676 A * | 8/1998 | Yoon | 604/167.03 |
| 5,904,703 A | 5/1999 | Gilson | |
| 5,906,577 A | 5/1999 | Beane et al. | |
| 6,048,309 A | 4/2000 | Flom et al. | |
| 6,562,022 B2 | 5/2003 | Hoste et al. | |
| 6,846,287 B2 * | 1/2005 | Bonadio et al. | 600/208 |
| 6,929,637 B2 | 8/2005 | Gonzalez et al. | |
| 6,958,037 B2 * | 10/2005 | Ewers et al. | 600/208 |
| 7,011,645 B2 | 3/2006 | McGuckin, Jr. et al. | |
| 7,300,399 B2 | 11/2007 | Bonadio et al. | |
| 7,473,221 B2 | 1/2009 | Ewers et al. | |
| 7,559,893 B2 | 7/2009 | Bonadio et al. | |

(Continued)

FOREIGN PATENT DOCUMENTS

| CA | 2702419 | | 11/2010 |
|---|---|---|---|
| CA | 2702419 | A1 | 11/2010 |

(Continued)

OTHER PUBLICATIONS

European Search Report 11194126.6-2310 dated Feb. 5, 2012.

(Continued)

*Primary Examiner* — Matthew Lawson
*Assistant Examiner* — Si Ming Lee

(57) ABSTRACT

A reinforced access assembly is provided. The access assembly includes a compressible body having proximal and distal ends and a substantially hourglass-shaped central portion extending therebetween. The compressible body defining at least a first lumen configured to receive an instrument in a sealing manner. The access assembly further includes a reinforcing mechanism extending between the proximal and distal ends of the compressible body. The reinforcing mechanism includes a plurality of rib members configured to permit compression of the compressible body during insertion into an incision and return the compressible body to an uncompressed condition following insertion.

19 Claims, 7 Drawing Sheets

(56) References Cited

U.S. PATENT DOCUMENTS

| | | |
|---|---|---|
| 7,758,500 B2 | 7/2010 | Boyd et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 8,157,786 B2 | 4/2012 | Miller et al. |
| 8,187,177 B2 | 5/2012 | Kahle et al. |
| 8,187,178 B2 | 5/2012 | Bonadio et al. |
| 8,323,184 B2 * | 12/2012 | Spiegal et al. ............... 600/206 |
| 8,465,422 B2 * | 6/2013 | Weisenburgh et al. ....... 600/217 |
| 2003/0014076 A1 | 1/2003 | Mollenauer et al. |
| 2003/0093104 A1 | 5/2003 | Bonner et al. |
| 2004/0054353 A1 | 3/2004 | Taylor |
| 2006/0071432 A1 * | 4/2006 | Staudner ...................... 277/630 |
| 2006/0149306 A1 | 7/2006 | Hart et al. |
| 2006/0161049 A1 * | 7/2006 | Beane et al. ................. 600/207 |
| 2006/0247500 A1 | 11/2006 | Voegele et al. |
| 2006/0247516 A1 | 11/2006 | Hess et al. |
| 2006/0247673 A1 | 11/2006 | Voegele et al. |
| 2006/0247678 A1 | 11/2006 | Weisenburgh, II et al. |
| 2006/0270911 A1 | 11/2006 | Voegele et al. |
| 2008/0021362 A1 * | 1/2008 | Fihe et al. .................... 602/75 |
| 2008/0097332 A1 | 4/2008 | Greenhalgh et al. |
| 2009/0093752 A1 * | 4/2009 | Richard et al. ............... 604/24 |
| 2010/0063452 A1 | 3/2010 | Edelman et al. |
| 2010/0152542 A1 * | 6/2010 | Hjelle et al. .................. 600/206 |
| 2010/0280326 A1 * | 11/2010 | Hess et al. .................... 600/206 |
| 2010/0298646 A1 | 11/2010 | Stellon et al. |
| 2011/0054260 A1 * | 3/2011 | Albrecht et al. ............. 600/208 |

FOREIGN PATENT DOCUMENTS

| | | |
|---|---|---|
| EP | 1312318 | 5/2003 |
| EP | 2226025 A1 | 9/2010 |
| EP | 2229900 | 9/2010 |
| EP | 2253283 | 11/2010 |
| WO | WO 2004/054456 A1 | 7/2004 |
| WO | WO2010/141409 | 12/2010 |

OTHER PUBLICATIONS

European Search Report for corresponding EP11250792 date of mailing is Feb. 24, 2012 (3 pgs).

* cited by examiner

REINFORCED FLEXIBLE ACCESS ASSEMBLY

CROSS REFERENCE TO RELATED APPLICATION

The present application claims the benefit of and priority to U.S. Provisional Application Ser. No. 61/416,517 filed on Nov. 23, 2010, the entire contents of which are incorporated herein by reference.

BACKGROUND

1. Technical Field

The present disclosure relates to a flexible access assembly for use in single incision surgical procedures. More particularly, the present disclosure relates to a reinforced flexible access assembly.

2. Background of Related Art

Access assemblies configured for reception through an incision into an abdominal cavity are known, as are methods of inserting the access assemblies therethrough. Traditional access assemblies include a rigid cannula that is received through the tissue of the body wall into the body cavity. Endoscopic, laparoscopic and other suitable instruments may then be directed through a housing on the proximal end of the cannula to access the body cavity in a sealing manner through the access assembly.

Compressible assemblies configured for accessing a body cavity and permitting reception of instruments therethrough in sealing manner are also known. Such compressible assemblies are composed of silicone, thermoplastic elastomers (TPE), rubber, foam, gel and other compressible materials and are configured to be compressed to facilitate insertion into an incision. Typically, such assemblies are deformed by a surgeon using his/her fingers or with the assistance of a grasping device, e.g., forceps. Compression of the assembly reduces the profile of the assembly, thereby facilitating reception of the assembly into the incision. Upon release of the compressive force, the compressed assembly returns to an uncompressed configuration. In the uncompressed configuration, the access assembly seals the incision into the body cavity. The assembly may have one or more access lumen for receiving instruments therethrough and may optionally be configured for connection with a source of insufflation gas.

Although configured to return to an uncompressed configuration once the compressive force is released, known compressible assemblies may fail to fully decompress. Additionally, known compressible assemblies may be subject to collapsing and/or excess flexion during use.

Therefore, it is desirable to provide a compressible access assembly which includes a reinforcing mechanism.

SUMMARY

Accordingly, a reinforced access assembly is provided. The access assembly includes a compressible body having proximal and distal ends and a substantially hourglass-shaped central portion extending therebetween. The compressible body defining at least a first lumen configured to receive an instrument in a sealing manner. The access assembly further includes a reinforcing mechanism extending between the proximal and distal ends of the compressible body. The reinforcing mechanism includes a plurality of rib members configured to permit compression of the compressible body during insertion into an incision and return the compressible body to an uncompressed condition following insertion.

In one embodiment, the access assembly further includes an upper rim at the proximal end of the body. Additionally, the access assembly may include a lower rim at the distal end of the body. Each of the plurality of rib members each may include a flange received within the upper rim and/or a flange received within the lower rim. Each of the flanges may include a lip for more securely receiving the rib members with the compressible body. The compressible body may include three lumen. The compressible body may be composed of at least one of silicone, thermoplastic elastomers (TPE), rubber, foam, gel. The reinforcing mechanism may further include one or more hoops.

DESCRIPTION OF THE DRAWINGS

Embodiments of a flexible access assembly are disclosed herein with reference to the drawings, wherein.

DETAILED DESCRIPTION

Embodiments of the presently disclosed access assembly will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user. Although the access assemblies of the present disclosure will be described as relates to accessing an abdominal cavity through an incision in the abdominal wall, the access assemblies of the present disclosure may be modified for use in other closed procedures, e.g., laparoscopic, arthroscopic, endoscopic. Furthermore, the access assemblies of the present disclosure may be modified for use in accessing internal cavities through natural orifices, e.g., anus, vagina.

Figure 1:
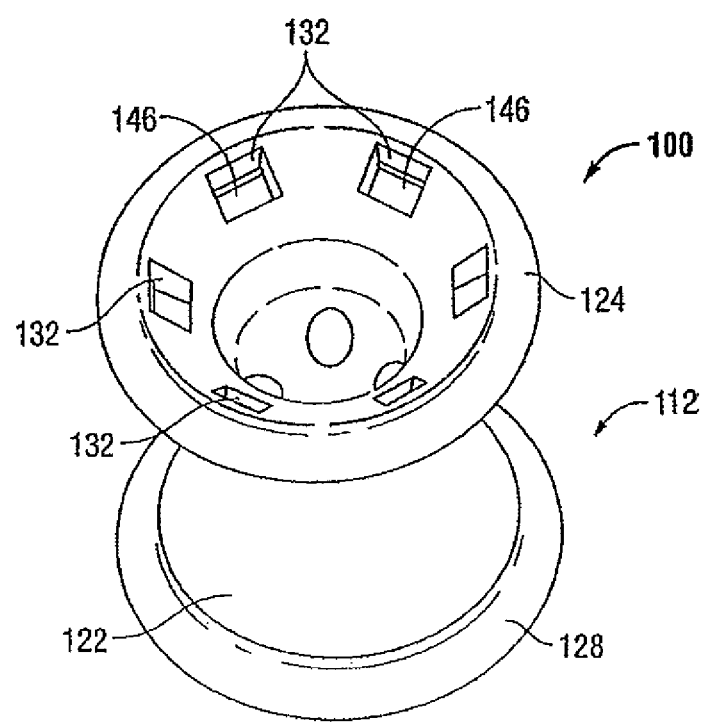
FIG. 1 is a perspective view of an embodiment of an access assembly according to the present disclosure.

Referring initially to FIG. 1, a reinforced access assembly according to an embodiment of the present disclosure is shown generally as access assembly 100. Access assembly 100 is flexible and/or compressible to allow for insertion through a single incision in the body of a patient such that after insertion, access assembly 100 creates a seal within the incision through which a surgeon may insert and manipulate one or more surgical instruments to complete a procedure.

With reference FIGS. 1-4, access assembly 100 includes a body 112 defining a substantially hourglass shape when viewed from the side. Body 112 includes a central portion 122 having an upper rim 124 located at a proximal end 126 of central portion 122 and a lower rim 128 located at a distal end 130 of central portion 122. Central portion 122 is configured to span the thickness of tissue "T" (FIG. 5). Upper rim 124 and lower rim 128 aid in preventing movement of access assembly 100 longitudinally through incision "I" (FIG. 5). As the thickness of tissue depends the body composition of the patient and the location through which the underlying cavity is being accessed, the length and size of access assembly 100 may be modified to suit a given procedure.

Still referring to FIGS. 1-4, body 112 of access assembly 100 may be formed of various materials such as, for example, silicone, thermoplastic elastomers (TPE), rubber, foam, gel, etc. In this manner, access assembly 100 may be compressed or squeezed prior to insertion through an incision or natural orifice in the body of a patient. In one embodiment, body 112 includes TPE material that is infused with an inert gas, e.g. $CO_2$ or Nitrogen, to form a foam structure. Body 112 may be coated with a lubricant, e.g. Parylene N or C, in order to create a lubricious surface. Various other coatings, e.g., hydrophilic, hydrophobic, bio-agents, anti-infection, analgesic, may also be employed to improve the access assembly or to adapt access assembly 100 for a specific procedure.

Figure 6:
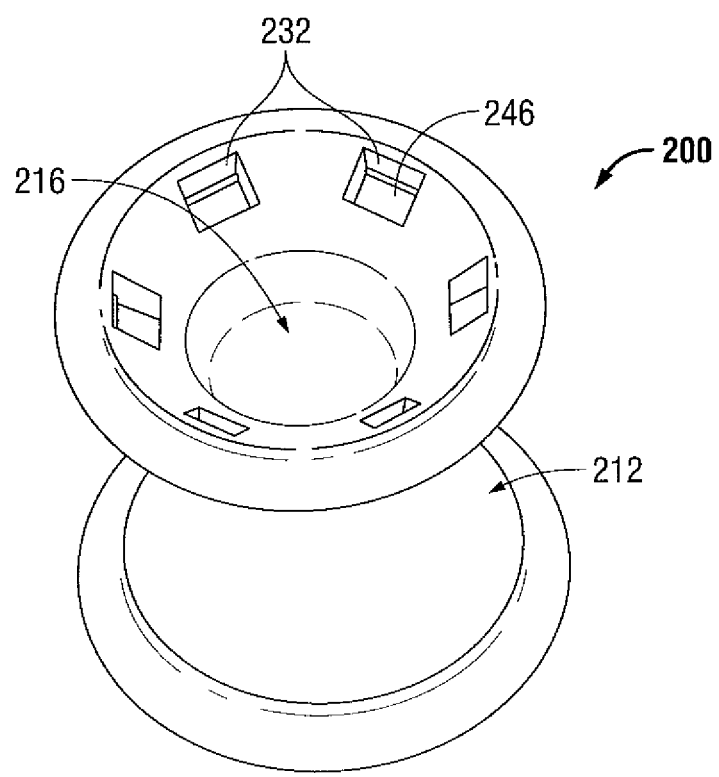
FIG. 6 is a perspective view of an access assembly according to an alternative embodiment of the present disclosure.

With reference still to FIGS. 1-4, body 112 of access assembly 100 defines a plurality of lumen 114, 116, 118. As shown, access assembly 100 includes three lumen 114, 116, 118 having substantially similar size and shape for receiving instruments of substantially similar diameter. Alternatively, one or more of lumens 114, 116, 118 may have a different size and shape for receiving an instrument of a different configuration. In one embodiment, body 112 may define a single lumen (FIG. 6) for receiving a single, large instrument. Lumens 114, 116, 118 extend through central portion 122 of body 112 and define longitudinal axes configured to receive surgical instruments, cannula assemblies, a valve assemblies and/or insufflation apparatus. Lumens 114, 116, 118 may include a protective lining (not shown) extending the length of central portion 122 to prevent tearing of access assembly 100 as instruments are manipulated therethrough. Lumen 114, 116, 118 may also be coated with a lubricant to assist in insertion of surgical instruments therethrough.

Still referring to FIGS. 1-4, access assembly 100 further includes a reinforcing mechanism 140 configured to add structural support to access assembly 100. Reinforcing mechanism 140 includes a plurality of flexible rib members 142 extending the length of body 112. As shown, reinforcing mechanism 140 includes six (6) rib members, although it is envisioned that reinforcing mechanism 140 may include fewer or more than six (6) rib members. Fewer rib members 142 provide access assembly 100 with more flexibility while limiting structural support. More rib members 142 provide access assembly 100 with increased structural support while limiting flexibility. Rib members 142 may be configured to increase hoop strength, to prevent collapse, and/or to assist in decompression of access assembly 100.

Figure 2:
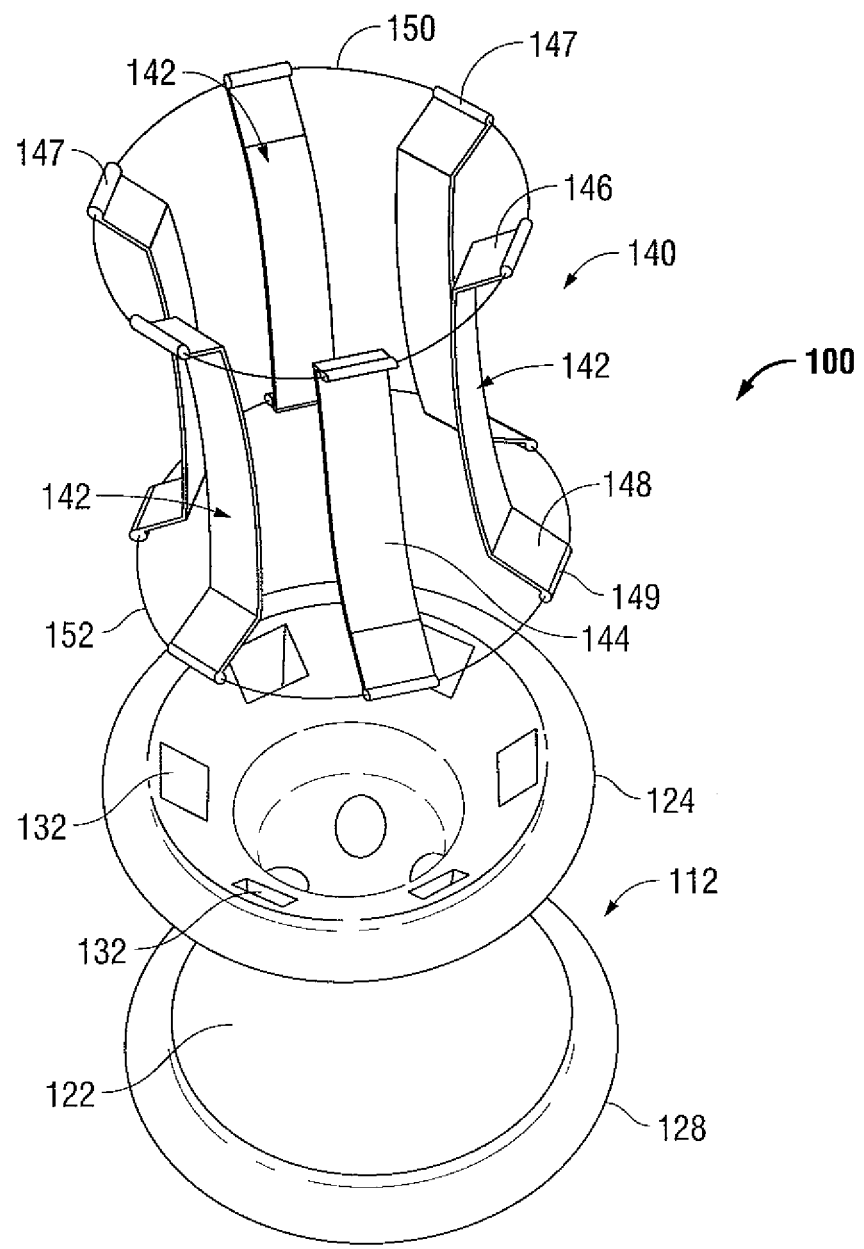
FIG. 2 is an exploded perspective view of the access assembly of FIG. 1.
Figure 3:
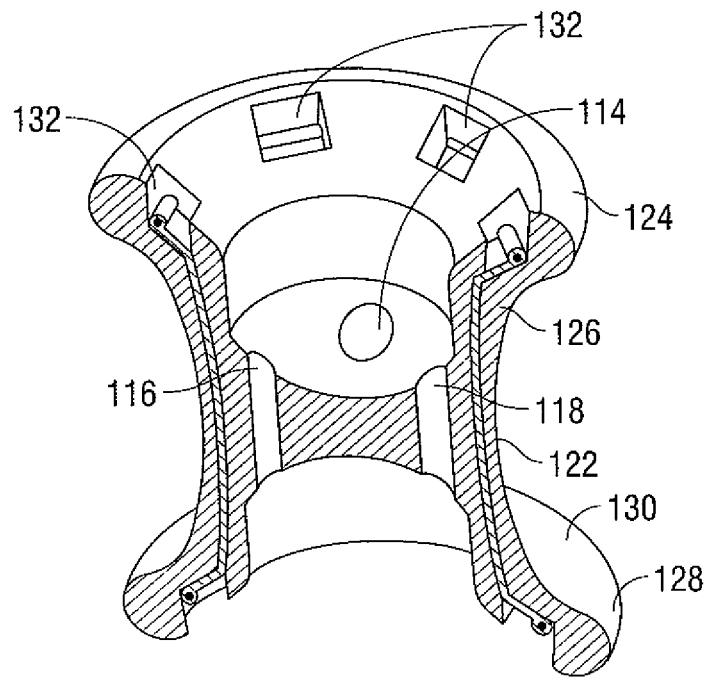
FIG. 3 is a perspective cross-sectional view of the access assembly of FIGS. 1 and 2.
Figure 4:
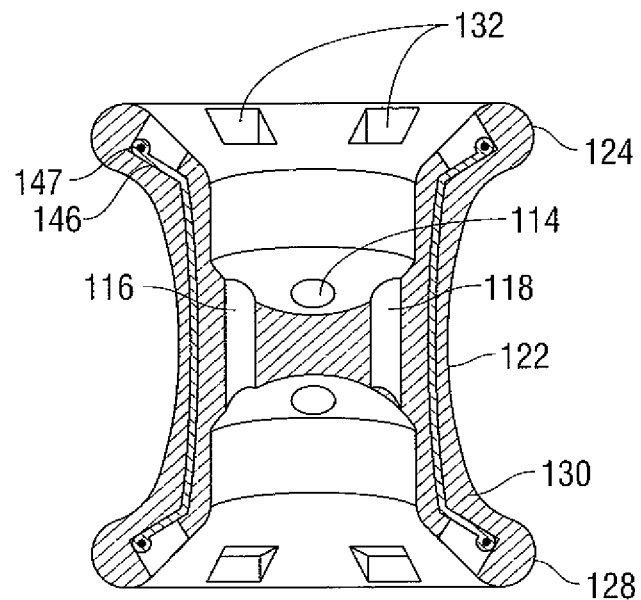
FIG. 4 is a cross-sectional side view of the access assembly of FIGS. 1-3.
Figure 5:
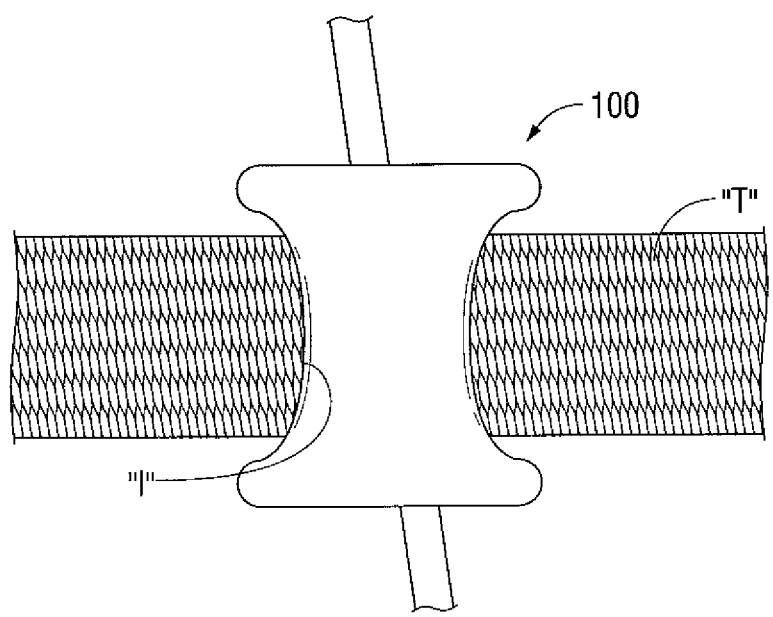
FIG. 5 is a partial cross-sectional view of the access assembly of FIGS. 1-4 positioned through an incision in tissue.

With particular reference to FIGS. 2-4, rib members 142 include a substantially planar base 144 having proximal and distal flanges 146, 148. Rib members 142 may be composed of plastic, polymer, metal, alloy or other suitable rigid or semi-rigid material. Rib members 142 are configured to permit the flexion and/or compression of body 112 of access assembly 100 during insertion of access assembly 100 and is configured to assist in the return of body 112 to an uncompressed configuration upon release of the compressive force. As such, rib members 142 operate in a spring-like manner to return access assembly 100 to an uncompressed configuration. The thickness and/or composition of rib members 142 may be modified to adjust the flexion characteristics of rib member 142. Each of rib members 142 may configured to have the same flexion characteristics, or instead, one or more of rib members 142 may be configured with different flexion characteristics. Base 144 extends the length of central portion 122 of body 112 such that proximal flange 146 is positioned within upper rim 124 of body 112 and distal flange 148 is positioned within lower rim 128 body 112. Each of proximal and distal flanges 146, 148 includes a lip member 147, 149 respectively. Lip members 147, 149 assist in anchoring rib members 142 within body 112. Depending on the material from which rib members 142 are constructed, rib members 142 may be bent, molded, milled or otherwise formed to the appropriate configuration.

With particular reference now to FIG. 2, optionally, reinforcing mechanism 140 includes a flexible hoop 150, 152, extending between each of proximal and distal flanges 146, 148, respectively, of rib members 142. Flexible hoops 150, 152 are configured to increase the hoop strength of access assembly 100 while permitting flexion and/or compression there of. Hoops 150, 152 may be composed of metal, alloy, plastic, polymer or other suitable flexible material. Although shown including only a single hoop on each of proximal and distal flanges 146, 148 of rib members 142, it is envisioned that reinforcing mechanism 140 may include one or more hoops spaced along base 144 of rib members 142.

In one embodiment, and as shown, access assembly 100 is formed or molded about reinforcing mechanism 140. Hoops 150, 152 may be added to rib members 142 prior to or following molding of body 112.

With reference to FIG. 5, reinforced access assembly 100 is configured to used in a traditional manner. Once an incision "I" is created through tissue "T", access assembly 100 is compressed to facilitate insertion of access assembly 100 through tissue "T". Once access assembly 100 is properly positioned within incision "I", release of the compressive force on access assembly 100 permits access assembly to return to the uncompressed or expanded configuration, as shown in FIG. 5, to create an opening through tissue "T" to permit sealed reception of one or more instruments through tissue "T" and into the body cavity of a patient. Upon completion of a procedure, flexible access assembly 100 is removed from within incision "I" through tissue "T" and the incision is closed in a conventional manner. While positioned through incision "I" in tissue "T", access assembly 100 may be used to complete any number of procedures.

Turning now to FIGS. 6-9, an alternative embodiment of an access assembly according to the present disclosure is shown generally as access assembly 200. Access assembly 200 is substantially similar to access assembly 100 described hereinabove, and will only be described as relates to the differences therebetween. Access assembly 200 includes a body 212 defining a single lumen 116.

Figure 7:
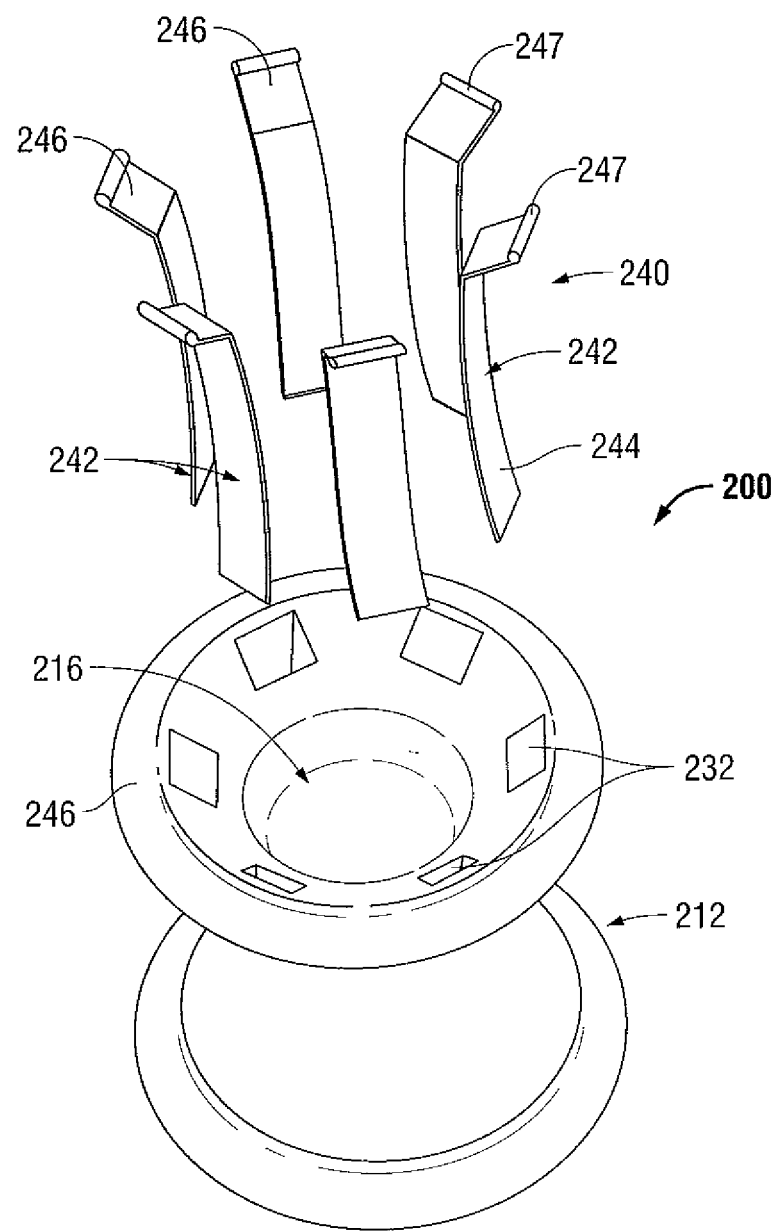
FIG. 7 is an exploded perspective view of the access assembly of FIG. 6.
Figure 8:
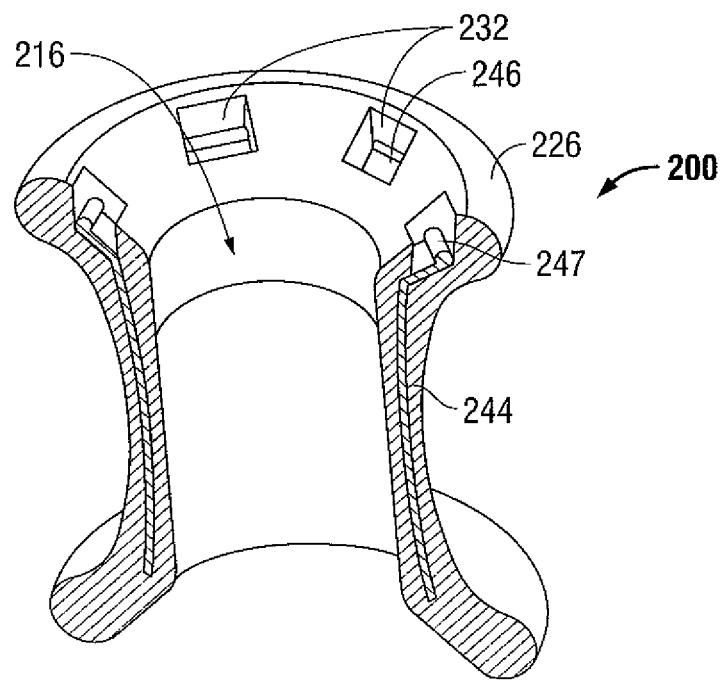
FIG. 8 is a perspective cross-sectional view of the access assembly of FIGS. 6 and 7.
Figure 9:
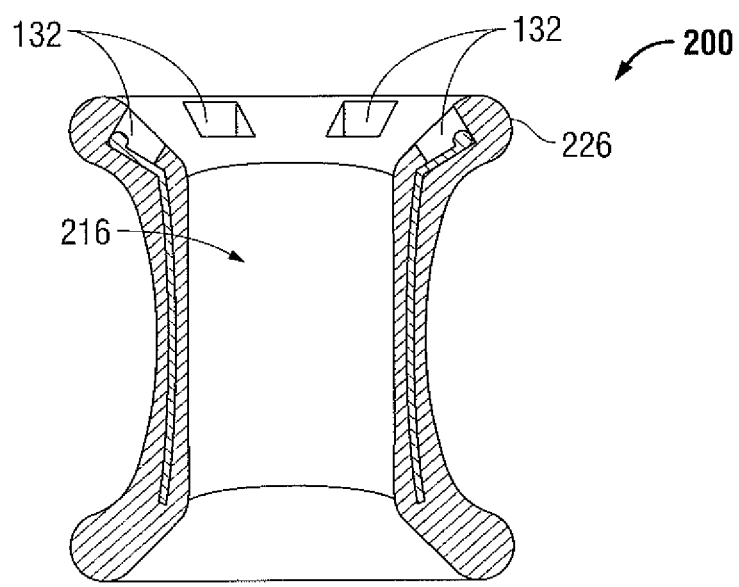
FIG. 9 is a cross-sectional side view of the access assembly of FIGS. 6 and 7.

With particular reference now to FIGS. 7-9, access assembly 200 further includes a reinforcing mechanism 240. Reinforcing mechanism 240 is substantially similar to reinforcing mechanism 140 described hereinabove. Reinforcing mechanism 240 includes rib members 242 including a substantially planar base 244 and a flange 246. Flange 246 may be located on the proximal and/or distal ends of planar base 244. Rib members 242 extend from a first rim 226 of body 212. First rim 226 may be located on either a proximal or distal end of body 212. Flange 246 includes a lip 247 to assist in securing rib member 242 within body 212.

With reference still to FIGS. 7-9, rib members 242 may be molded within body 212 of access assembly 200, as discussed above with regards to access assembly 100. Alternatively, access assembly 200 is molded to included openings 232 in body 212. Rib members 242 are then received within openings 232 to reinforce body 212. In this manner, the size and thickness of rib members 242 may be determined by a clinician prior to use.

It will be understood that various modifications may be made to the embodiments disclosed herein. For example, as noted hereinabove, the disclosed flexible access assembly may be provided with multiple lumen in excess of the disclosed three lumen. Additionally, the diameters or configuration of the disclosed lumen need not be identical but may be varied depending upon the contemplated surgical instruments to be utilized therethrough. Therefore, the above description should not be construed as limiting, but merely as exemplifications of particular embodiments. Those skilled in the art will envision other modifications within the scope and spirit of the claims appended hereto.

The invention claimed is:

1. An access assembly comprising:
a compressible body having proximal and distal ends and an hourglass-shaped central portion extending therebetween, the compressible body defining at least a first lumen configured to receive an instrument in a sealing manner when the instrument is received through the at least first lumen, the compressible body defining at least one channel between the proximal and distal ends, the at least one channel enclosed within a wall of the central portion, wherein the at least one channel defines an opening in at least one of the proximal and distal ends; and
a reinforcing mechanism selectively insertable into the at least one channel and extending between the proximal and distal ends of the compressible body, the reinforcing mechanism including a plurality of rib members configured to permit compression of the compressible body during insertion into an incision and return the compressible body to an uncompressed condition following insertion, wherein the reinforcing mechanism is maintained entirely within the compressible body when the reinforcing mechanism is received within the at least one channel.

2. The access assembly of claim 1, further including an upper rim at the proximal end of the body.

3. The access assembly of claim 2, further including a lower rim at the distal end of the body.

4. The access assembly of claim 2, wherein each of the plurality of rib members includes a flange received within the upper rim.

5. The access assembly of claim 3, wherein each of the plurality of rib members includes a flange received within the lower rim.

6. The access assembly of claim 3, wherein each of the plurality of rib members includes a first flange located in the proximal end of the body and a second flange located in the distal end of the body.

7. The access assembly of claim 4, wherein each of the flanges includes a lip for more securely receiving the rib members within the compressible body.

8. The access assembly of claim 5, wherein each of the flanges includes a lip for more securely receiving the rib members within the compressible body.

9. The access assembly of claim 6, wherein each of the flanges includes a lip for more securely receiving the rib members within the compressible body.

10. The access assembly of claim 1, wherein the compressible body includes three lumen.

11. The access assembly claim 1, wherein the compressible body is composed of at least one of silicone, thermoplastic elastomers (TPE), rubber, foam, or gel.

12. The access assembly of claim 1, wherein the reinforcing mechanism further includes one or more holes configured to accept one or more hoops.

13. An access assembly comprising:
a compressible body having proximal and distal ends and an hourglass-shaped central portion extending therebetween, the compressible body defining at least a first lumen configured to receive an instrument in a sealing manner, wherein the compressible body forms a seal about the instrument when the instrument is received through the at least first lumen, the compressible body defining a plurality of channels between the proximal and distal ends, the channels enclosed within a wall of the central portion; and
a reinforcing mechanism extending between the proximal and distal ends of the compressible body and maintained entirely within the compressible body, the reinforcing mechanism including a plurality of rib members configured to permit compression of the compressible body during insertion into an incision and return the compressible body to an uncompressed condition following insertion, wherein each of the plurality of rib members includes at least one flange received within a proximal rim of the proximal end of the compressible body, and each of the rib members disposed in one of the channels.

14. An access assembly comprising:
a compressible body having proximal and distal ends and an hourglass-shaped central portion extending therebetween, the compressible body defining at least a first lumen configured to receive an instrument in a sealing manner, the compressible body defining a plurality of channels between the proximal and distal ends, each channel enclosed within a wall of the central portion; and
a reinforcing mechanism extending between the proximal and distal ends of the compressible body and maintained entirely within the compressible body, the reinforcing mechanism including a plurality of rib members configured to permit compression of the compressible body to a compressed condition during insertion of the compressible body into an incision and expands the compressible body to an uncompressed condition following insertion of the compressible body within the incision, each rib member disposed in one of the channels, wherein the reinforcing mechanism further includes at least one wire hoop connecting each of the plurality of rib members.

15. The access assembly of claim 14, wherein a first wire hoop extends between each of the plurality of rib members.

16. The access assembly of claim 14, wherein the first wire hoop connects a proximal end of each of the plurality of rib members and a second wire hoop connects a distal end of each of the plurality of rib members.

17. An access assembly comprising:
a compressible body having a proximal end and a distal end and an hourglass-shaped central portion extending therebetween, the compressible body defining a plurality of lumens each configured to receive an instrument in a sealing manner, the compressible body defining a plurality of channels between the proximal end and the distal end, the plurality of channels being enclosed within a wall of the central portion, wherein the plurality of channels each defines an opening in one of the proximal end and the distal end; and
a reinforcing mechanism including a plurality of rib members removable from within the plurality of channels and extending between the proximal end and the distal end of the compressible body, the reinforcing member configured to permit compression of the compressible body during insertion into an incision and return the compressible body to an uncompressed condition following insertion, wherein the reinforcing mechanism is maintained entirely within the compressible body when the reinforcing mechanism is received within the plurality of channels.

18. The access assembly of claim 17, further including an upper rim at the proximal end of the body and a lower rim at the distal end of the body.

19. The access assembly of claim 18, wherein each of the plurality of rib members includes a flange received within one of the upper rim and the lower rim.

* * * * *